United States Patent
Katcha et al.

(10) Patent No.: US 7,197,113 B1
(45) Date of Patent: Mar. 27, 2007

(54) CONTACTLESS POWER TRANSFER SYSTEM

(75) Inventors: Jason Stuart Katcha, Whitefish Bay, WI (US); Jonathan Richard Schmidt, Wales, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/292,244

(22) Filed: Dec. 1, 2005

(51) Int. Cl.
*H05G 1/10* (2006.01)
*H05G 1/12* (2006.01)
*H05G 1/00* (2006.01)

(52) U.S. Cl. .......................... 378/101; 378/104; 378/4

(58) Field of Classification Search .................... 378/4, 378/15, 101–118; 336/120–129
See application file for complete search history.

(56) References Cited

U.S. PATENT DOCUMENTS

| | | |
|---|---|---|
| 4,672,528 A | 6/1987 | Park et al. |
| 4,912,735 A | 3/1990 | Beer |
| 5,451,878 A | 9/1995 | Wirth et al. |
| 5,608,771 A | 3/1997 | Steigerwald et al. |
| 5,646,835 A | 7/1997 | Katcha |
| 6,674,836 B2 | 1/2004 | Harada et al. |
| 2004/0264642 A1 | 12/2004 | Katcha et al. |
| 2006/0022785 A1* | 2/2006 | Dobbs .......................... 336/120 |

* cited by examiner

*Primary Examiner*—Edward J. Glick
*Assistant Examiner*—Irakli Kiknadze
(74) *Attorney, Agent, or Firm*—Michael Della Penna; Dean D. Small; Small Patent Law Group

(57) ABSTRACT

In accordance with one embodiment, a contactless power transfer system is provided that comprises a stationary member including a power input configured to receive power at first voltage from a power supply. The system further includes a rotating member rotatably coupled to the stationary member and a rotary transformer. The rotary transformer has primary and secondary sides, with the primary side being disposed on the stationary member. The primary side has a primary winding that receives power at the first voltage from the power input. The secondary side is disposed on the rotating member and produces power at a second voltage. The secondary side has a rotating core and separate secondary sub-windings, each of which has forward and return paths that are circumferentially disposed about the rotating core. The forward and return paths of each of the sub-windings rotate proximate to, and are disposed a substantially equal distance from, the primary winding disposed on the stationary member.

36 Claims, 10 Drawing Sheets

CONTACTLESS POWER TRANSFER SYSTEM

BACKGROUND OF THE INVENTION

Embodiments of the present invention relate generally to power transfer mechanisms and, more particularly, to a contactless power transfer system.

High-voltage power transformers are used in a variety of applications, such as in baggage scanner systems, computed tomography (CT) systems and the like. CT systems are often used to obtain non-invasive sectional images of test objects, particularly internal images of human tissue for medical analysis and treatment. Current baggage scanner systems and CT systems position the test object, such as luggage or a patient, on a conveyor belt or table within a central aperture of a rotating frame which is supported by a stationary frame. The rotating frame includes an x-ray source and a detector array positioned on opposite sides of the aperture, both of which rotate around the test object being imaged. At each of several angular positions along the rotational path (also referred to as "projections"), the x-ray source emits a beam that passes through the test object, is attenuated by the test object, and is received by the detector array. The x-ray source utilizes high-voltage power to generate the x-ray beams.

Each detector element in the detector array produces a separate electrical signal indicative of the attenuated x-ray beam intensity. The electrical signals from all of the detector elements are collected and processed by circuitry mounted on the rotating frame to produce a projection data set at each gantry position or projection angle. Projection data sets are obtained from different gantry angles during one revolution of the x-ray source and detector array. The projection data sets are then processed by a computer to reconstruct the projection data sets into an image of a bag or a CT image of a patient.

The circuitry mounted on the rotating frame is powered by low-voltage power, while the x-ray source is powered by high-voltage power. Conventional rotating gantry based systems utilize a brush and slip ring mechanism to transfer power at a relatively low-voltage between the stationary and rotating portions of the gantry frame. The rotating gantry portion has an inverter and high-voltage tank mounted thereon and connected to the brush and slip ring mechanism. The inverter and high-voltage tank including transformer, rectifier, and filter capacitance components that step-up the voltage from the low-voltage, transferred through the brush and slip ring mechanism, to the high-voltage needed to drive the x-ray source. The transformer in the high-voltage tank produces a high-voltage AC signal which is converted to a high-voltage DC signal by rectifier circuits inside the high-voltage tank.

However, rotating gantry based scanner systems have experienced certain disadvantages. The high-voltage tank and inverter on the rotating gantry portion increases the weight, volume and complexity of the system. Furthermore, the brush and slip ring mechanisms (which are typically used to carry appreciable current) are subject to reduced reliability, maintenance problems, and electrical noise generation, which interfere with sensitive electronics. As systems are developed that rotate faster, it becomes advantageous to reduce the volume and weight of the rotating components.

Accordingly, it is desirable to provide a mechanism for transferring power from a stationary power supply to a rotational load (e.g., in a baggage scanner or CT system) in a contactless manner, e.g., without the need for a brush and slip ring mechanism. It is also desirable to reduce the weight and complexity of the rotational gantry portion of the scanner or system while increasing the reliability of the power transfer mechanism

BRIEF SUMMARY OF THE INVENTION

In accordance with one embodiment, a contactless power transfer system is provided that comprises a stationary member including a power input that is configured to receive power at a first voltage from a power supply. The system further includes a rotating member rotatably coupled to the stationary member and a rotary transformer. The rotary transformer has primary and secondary sides. The primary side is disposed on the stationary member and has a primary winding that receives power at the first voltage from the power input. The secondary side is disposed on the rotating member and produces power at a second voltage. The secondary side has a rotating core and separate secondary sub-windings, each of which has forward and return paths that are circumferentially disposed about the rotating core. The forward and return paths of each of the sub-windings rotate proximate, to and are disposed a substantially equal distance from, the primary winding disposed on the stationary member.

Optionally, a high-voltage component may be disposed on the rotating member, with the secondary side providing power at a high-voltage to the high-voltage component. In addition, a low-voltage component may be disposed on the rotating member, with the secondary side providing power at a low-voltage to the low-voltage component. Optionally, the rotating core may include an E-shaped cross-section divided into arcuate sections, such that each of the sub-windings is wrapped about a separate and corresponding one of the arcuate sections. Optionally, each sub-winding may be formed as a closed loop that is entirely contained within an arcuate section of the rotating core. Each closed loop may include opposite ends that are located proximate corresponding opposite ends of adjacent sub-windings. Each of the sub-windings may extend over a separate and independent arcuate section of the stationary core.

In accordance with at least one embodiment, separate signal conditioning modules are included within the system and joined to output leads of corresponding sub-windings. The signal conditioning modules may include rectifier and/or doubler circuits that are disposed on and distributed evenly about the rotating member.

In accordance with an alternative embodiment, an x-ray scanning system is provided that includes a gantry that supports a stationary member and that rotatably couples a rotating member relative to the stationary member. The system may further include an x-ray source provided on the rotating member and a rotary transformer having primary and secondary sides disposed on the stationary and rotating members, respectively. The primary side is disposed on the stationary member and has a primary winding that receives power at the first voltage from the power input. The secondary side is disposed on the rotating member and produces power at a second voltage. The secondary side has a rotating core and separate secondary sub-windings, each of which has forward and return paths that are circumferentially disposed about the rotating core. The forward and return paths of each of the sub-windings rotate proximate to, and are disposed a substantially equal distance from, the primary winding disposed on the stationary member.

DETAILED DESCRIPTION OF THE INVENTION

The terms "low-voltage" and "high-voltage" as used throughout are not intended to represent absolute valves, but instead are intended merely to indicate a relative relation to one another.

Figure 1:
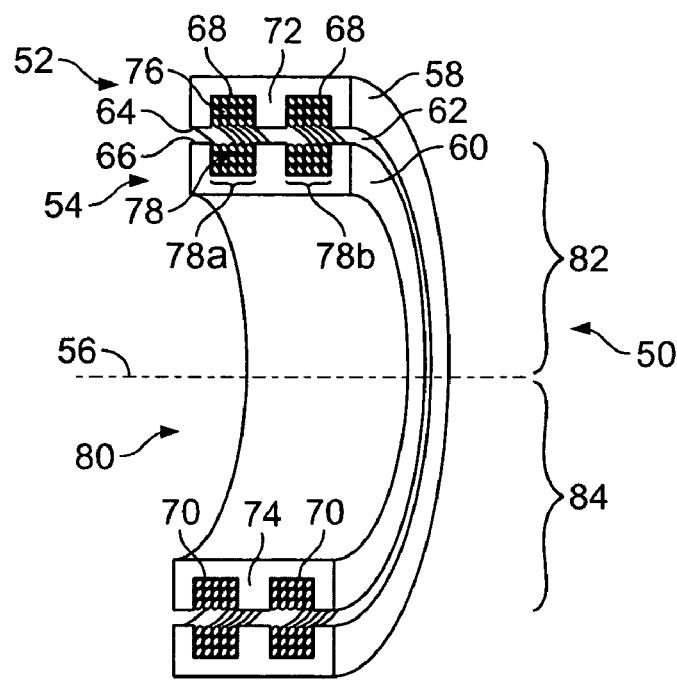
FIG. 1 illustrates a rotary transformer for a contactless power transfer system formed in accordance with one embodiment of the present invention.

FIG. 1 illustrates a contactless power transfer system 50 formed in accordance with an embodiment of the present invention. The system 50 includes a stationary member 52 and a rotating member 54 located proximate one another and in a concentric arrangement about axis 56. The rotating member 54 rotates about axis 56 relative to the stationary member 52. By way of example, the stationary member 52 may simply represent a stator, while the rotating member 54 may represent a rotor, both of which may be coupled to a common framework, such as a gantry (e.g., see FIGS. 10 and 12). The stationary member 52 has a stationary core 58, while the rotating member 54 has a rotating core 60. The stationary and rotating cores 58 and 60 have corresponding inner and outer surfaces 64 and 66, respectively. The inner and outer surfaces 64 and 66 are separated by an air gap 62, are directed toward one another and rotate in close proximity to one another.

The stationary and rotating cores 58 and 60 have E-shaped cross sections aligned with, opening toward one another, and extending in a cylindrical or tubular manner about the axis 56. The E-shaped cross-section in the stationary core 58 includes parallel winding slots 68 cut in the inner surface 64 and separated by a middle leg 72. The winding slots 68 and middle leg 72 face inward toward, and extend in a circumferential direction about, the axis 56. The rotating core 60 includes parallel winding slots 70 cut in the outer surface 66 and separated by a middle leg 74. The winding slots 70 and middle leg 74 face outward away from, and extend in a circumferential direction about, the axis 56.

The stationary core 58 receives a primary winding 76 that is provided within the winding slots 68 and wrapped about the middle leg 72. The primary winding 76 loops about the complete circumference of the inner surface 64 within the winding slots 68. The primary winding 76 is wound in one direction in one of winding slots 68 and loops back in the opposite direction in the other of winding slots 68. The rotating core 60 receives a secondary winding 78 that are provided within the winding slots 70 and wrapped about segments of the middle leg 74. The secondary winding 78 is divided into separate sub-windings that loop or wrap in opposite directions within the secondary winding slots 70. The rotating core 60 and secondary windings 78 are divided into arcuate sections 82 and 84. Each arcuate section 82 and 84 includes a separate and independent secondary sub-winding. Each secondary sub-winding includes a forward path 78a and a return path 78b. The forward and return paths 78a and 78b are spaced a substantially equal distance from the primary winding 68. The distance between the primary winding 68 and forward and return paths 78a and 78b corresponds to a thickness or width of the air gap 62. The forward and return paths 78a and 78b are arranged in a common curved or cylindrical plane defined by and following a contour of the outer surface 66 of the rotating core 60. In the example of FIG. 1, half of the stationary rotating members 52 and 54 are shown, but it is understood that the other similarly structured. Thus, in the example of FIG. 1, the rotating core 60 includes four arcuate sections, each comprising approximately 90° of the rotating core 60.

The external magnetic fields are very small at some distance form the cores, thereby limiting magnetic and electrical interference with rotating electronics including the data acquisition system. The magnetic fields are small at some distance from the cores due to the magnetic field cancellation between the primary and secondary windings 76 and 78. The magnetic field cancellation in the E-shaped core configuration is achieved by locating the return path of the primary and each secondary sub-windings immediately adjacent one another, and the planes (flat or curved) formed by the primary and secondary windings face each other separated only by the air gap 62.

Figure 2:
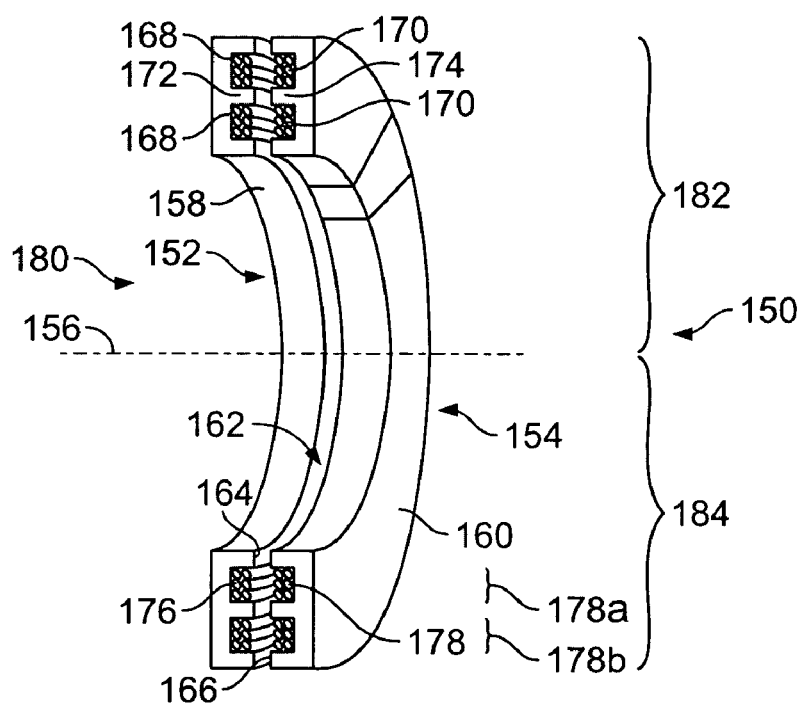
FIG. 2 illustrates a rotary transformer for a contactless power transfer system formed in accordance with an alternative embodiment of the present invention.

FIG. 2 illustrates a contactless power transfer system 150 formed in accordance with an alternative embodiment. The system 150 includes a stationary member 152 and a rotating member 154 located proximate one another and in facing parallel planes extending perpendicular to an axis 156. The rotating member 154 rotates relative to the stationary member 152 about axis 156 and within a plane aligned parallel to a plane containing the stationary member 152. By way of example, the stationary member 152 may simply represent a stator, while the rotating member 154 may represent a rotor. The stationary member 152 has a stationary core 158, while the rotating member 154 has a rotating core 160. The stationary and rotating cores 158 and 160 are separated by an air gap 162 and have an open facing sides 164 and 166, respectively, that are directed toward one another and rotate in close proximity to one another. The stationary and rotating cores 158 and 160 extend along corresponding parallel planes.

The stationary and rotating cores 158 and 160 have E-shaped cross sections aligned with and facing one another. The E-shaped cross-section in the stationary core 158 includes parallel winding slots 168 cut in the side 164 and separated by a middle leg 172. The winding slots 168 and middle leg 172 extend about the axis 156 and lie within the plane containing the stationary core 158. The rotating core 160 includes parallel winding slots 170 cut in the side 166 and separated by a middle leg 174. The winding slots 170 and middle leg 174 extend about the axis 156 and lie within the plane containing the stationary core 160.

The stationary core 158 receives a primary winding 176 that is provided within the winding slots 168 and wrapped about the middle leg 172. The primary winding 176 extends along the side 164 about the axis 156 and is aligned with the plane containing the stationary core 158. The primary winding 176 is wound in one direction in one of winding slots 168 and loops back to return in the opposite direction in the other of winding slots 168. The rotating core 160 receives secondary winding 178 that is provided within the winding slots 170 and wrapped about segments of the middle leg 174. The secondary windings 178 are wound in opposite directions in the secondary winding slots 170. The rotating core 160 and secondary windings 178 are divided into arcuate sections 182 and 184. Each arcuate section 182 and 184 includes a separate and independent secondary sub-winding (as will be described more below). Each secondary sub-winding 178 includes a forward path 178a and a return path 178b. The forward and return paths 178a and 178b are spaced a substantially equal distance (corresponding to the width of the air gap 162) from the primary winding 176. The forward and return paths 178a and 178b are aligned in a common flat plane defined by and following the side 166 of the rotating core 160.

As explained above in connection with FIG. 1, the external magnetic fields are very small at some distance from the rotating core 160. In the configuration of FIG. 2, the magnetic fields are small at some distance from rotating cores due to the magnetic field cancellation between the primary and secondary windings 176 and 178. The magnetic field cancellation in the E-core configuration is quite substantial given that the configuration locates the return path of the primary and secondary windings adjacent one another and separated only by the air gap 162.

Figure 3:
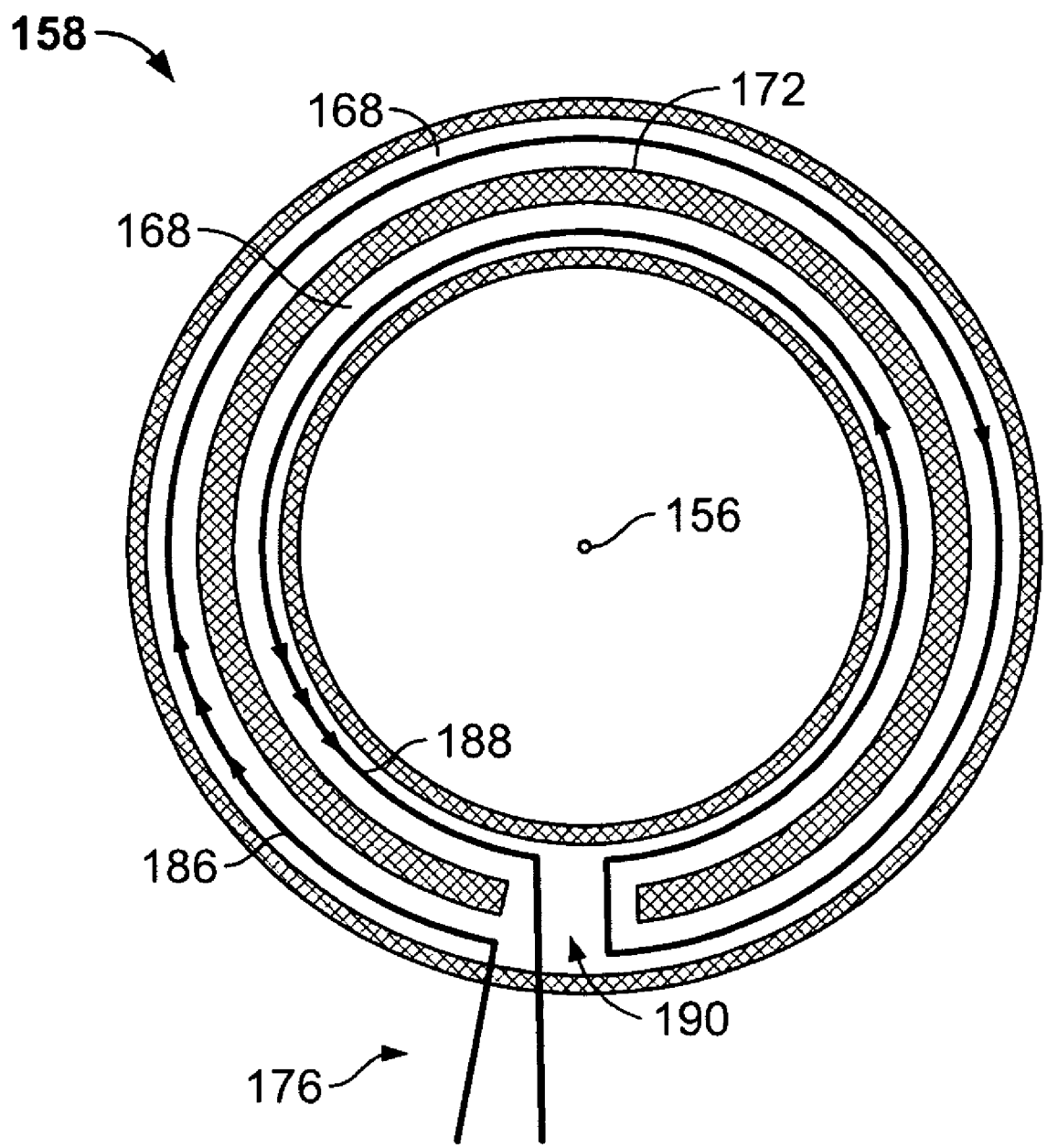
FIG. 3 illustrates the primary winding of the rotary transformer of FIG. 2.

FIG. 3 illustrates a front view of the stationary core 158 of the contactless power transfer system 150 of FIG. 2. FIG. 3 better illustrates the stationary core 158 and the winding slots 168. The winding slots 168 are separated by the middle leg 172. The winding slots 168 and middle leg 172 are arranged as concentric circles about the rotation axis 156 (denoted as a single point extending out of the page in FIG. 3) and are aligned in a common plane (represented by the plane of the page in FIG. 3). The primary winding 176 includes a first portion or partial loop 186 extending in the direction denoted by arrows in FIG. 3 and a second portion or partial loop 188 extending in the opposite direction denoted by arrows as well. The middle leg 172 has a bridge cutout 190 cut there through and extending between the winding slots 168. The cutout 190 enables transition of the primary winding 176 between the inner and outer winding notches 168 to form a closed loop. While a single line is illustrated within FIG. 3 as the primary winding 176, it is understood that multiple individual wires may be wrapped within the winding slots 168 to collectively define the primary winding 176.

Figure 4:
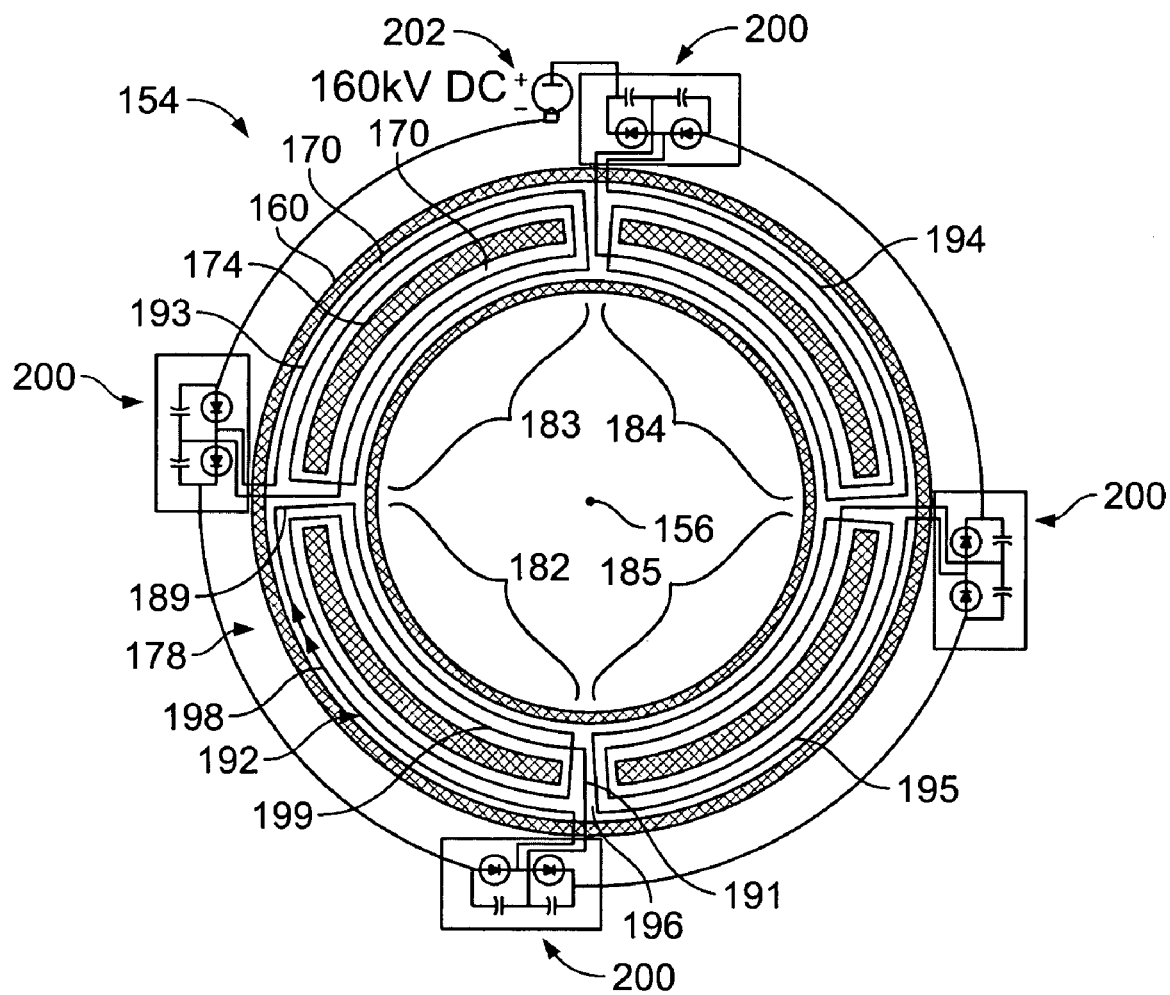
FIG. 4 illustrates the secondary winding of the rotary transformer of FIG. 2.

FIG. 4 illustrates a front view of the rotating core 160 of the contactless power transfer system 150 of FIG. 2, along with schematic representations of signal conditioning modules 280 provided on the rotating member 154 (FIG. 2). FIG. 4 better illustrates the rotating core 160 and the winding slots 170. The winding slots 170 are separated by the middle leg 174 and are arranged in concentric circles about the rotation axis 156 (denoted as a single point extending out of the page in FIG. 4). The winding slots 170 and middle leg 174 are arranged in a common flat or curved plane (represented by the plane of the page in FIG. 4). The middle leg 174 is segmented into adjacent arcuate sections 182–185.

The secondary winding 178 includes separate and independent sub-windings 192–195 that are located in the discrete, adjacent arcuate sections 182–185. Each arcuate section 182–185 includes a portion of the middle leg 174 separated by bridge cutouts 196. Each arcuate section 182–185 includes a corresponding one of sub-windings 192. Each sub-winding 192 forms a closed loop with a first portion 198 (corresponding to the forward path) extending in the direction denoted by arrows and a second portion 199 (corresponding to the return path) extending in the direction denoted by arrows with opposite ends 189 and 191. The direction of current flow may be reversed. Each closed loop is entirely contained within an arcuate section 182–185. The closed loop of each sub-winding 192 has opposite ends 189 and 191 located proximate ends 189 and 191 of adjacent sub-windings 192. In the example of FIG. 4, each sub-winding 192 extends over a separate and independent arcuate section 182–185 of the rotating core 160. Also, the sub-windings 192 follow an oval or elliptical path centered at the axis 156. Optionally, the windings 192 may overlap one another, and/or be oriented in a flared or spiral manner. For example, a spiral arrangement would locate one end 189 closer to the axis 156 and the sub-winding 192 would spiral away from the axis 156 as the sub-winging 192 curves about the axis 156. The end 191 would be positioned radially further from axis 156 than end 189.

Each sub-winding 192 is joined to a corresponding signal conditioning module 200. By way of example, each signal conditioning module 200 may include a rectifier, a voltage double and the like. The signal conditioning modules 200 are provided on, and distributed about, the rotating member 154 and are electrically coupled to output leads of corresponding sub-windings 192. The signal conditioning modules 200 are electrically joined to one another in series, to collectively produce a high-voltage output 202. In the example of FIG. 4, the signal conditioning modules 200 include rectifier and doubler circuits that collectively produce the high-voltage output 202 (e.g. a 160 kV DC signal).

In the example of FIG. 4, the arcuate sections 182–185 are positioned at evenly spaced 90° increments about the middle leg 174. Optionally, the arcuate sections 182–185 may be different in size/length relative to one another. Alternatively, fewer or more than four sections 182–185 may be utilized.

Figure 5:
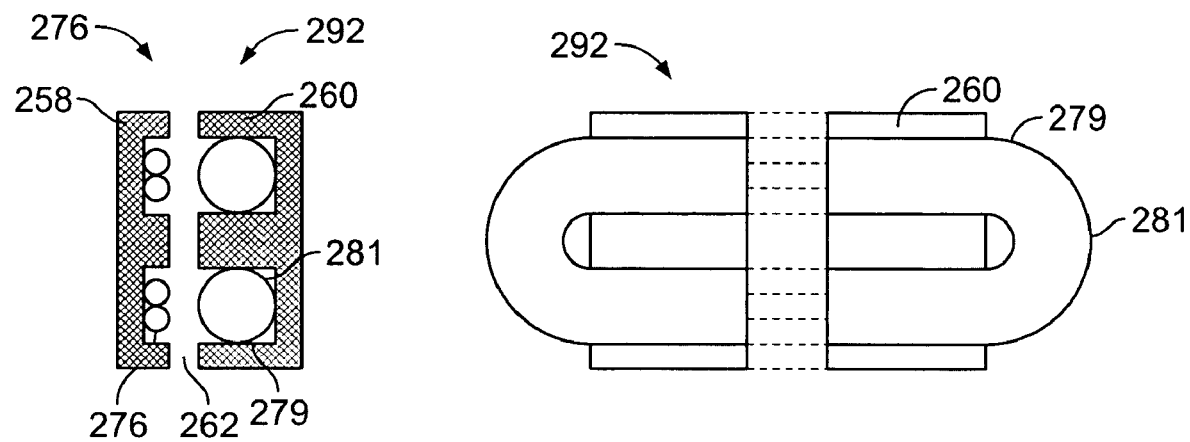
FIG. 5 illustrates front and cross-sectional layouts for a simplified secondary winding formed in accordance with an embodiment of the present invention.

FIG. 5 illustrates a cross-sectional layout of a simplified primary winding 276 and a single secondary sub-winding 292 arranged in parallel planes, as well as a front view of the secondary sub-winding 292. The secondary sub-winding 292 is held in an arcuate portion of a rotating core 260 in close proximity to the primary winding 276. The secondary winding 278 includes a conductive wire 279 surrounded by high-voltage insulation 281. One or more loops of the wire 279 and insulation 281 may form the sub-winding 292. As the rotating core 260 rotates relative to the stationary core 258, the primary winding 276 and secondary sub-winding 292 remain in close proximity to one another, separated only by the air gap 262.

Figure 6:
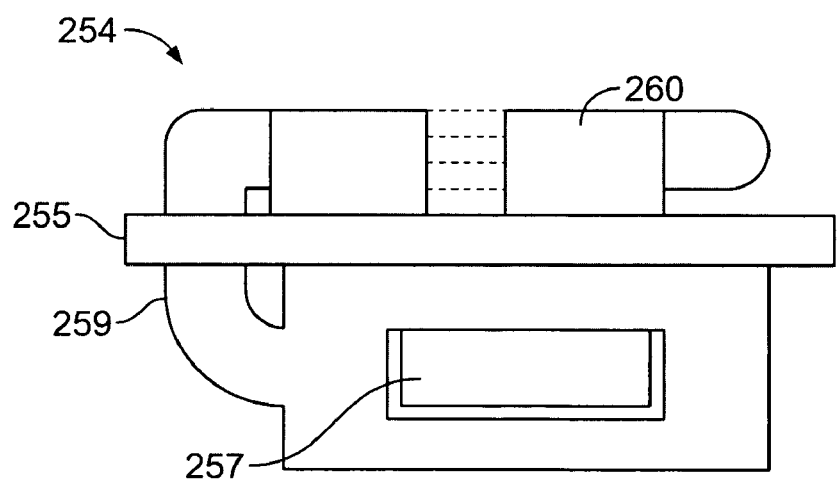
FIG. 6 illustrates a side sectional view of a secondary winding and rectifier/doubler module formed in accordance with an embodiment of the present invention.

FIG. 6 illustrates a side view of a rotating member 254 that includes a platter 255 with the rotating core 260 mounted thereon. The rotating core 260 is provided on a first side of the platter 255, while a signal conditioning module 257 is provided on the opposite side of the platter 255. The signal conditioning module 257 is joined to the secondary sub-winding 292 through sub-winding output leads 259. By way of example, the voltage provided over the sub-winding output leads 259 may be 40 kV AC, which is then converted by the signal conditioning module 257 to 40 kV DC.

Figure 7:
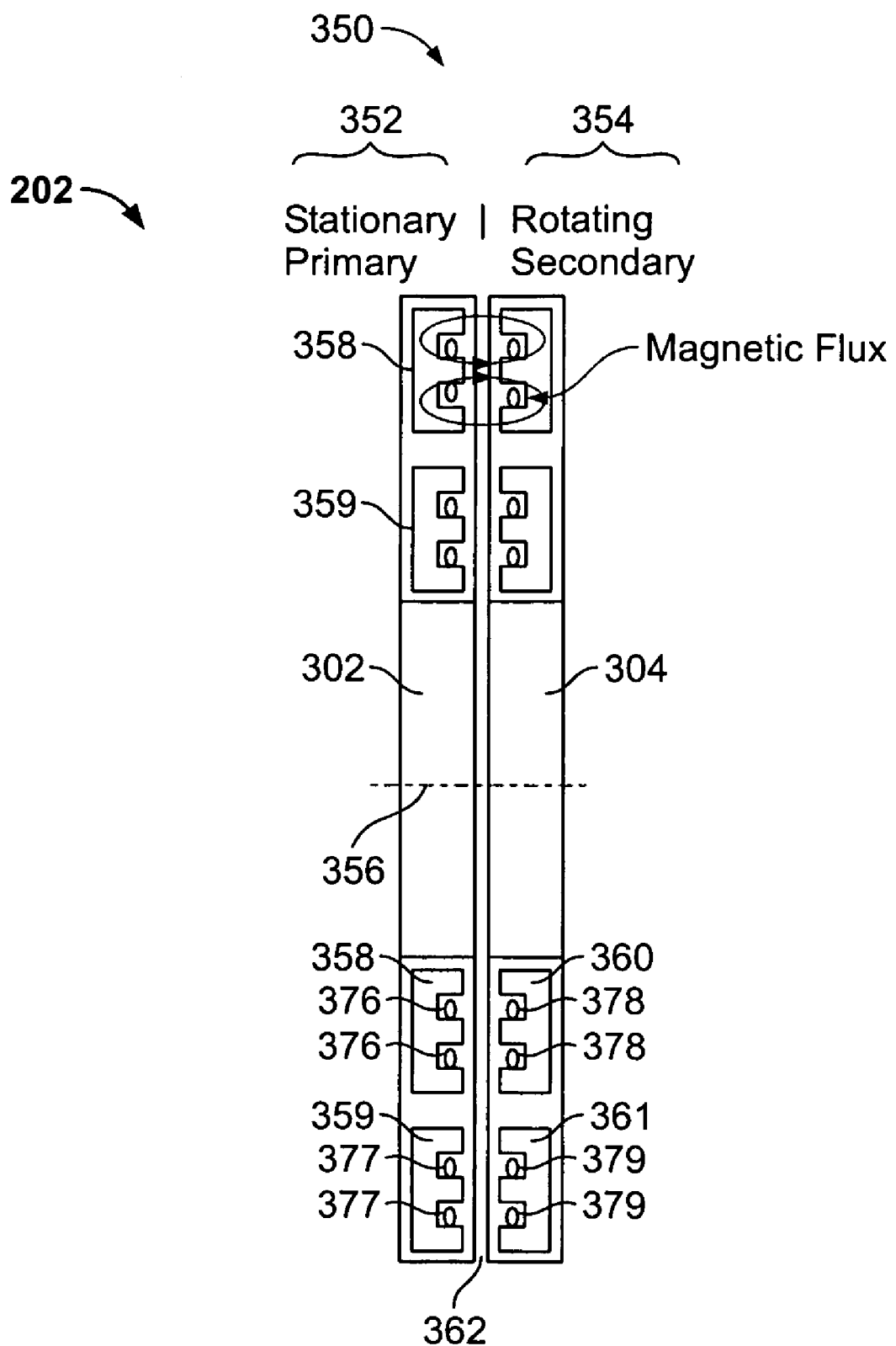
FIG. 7 illustrates a rotary transformer for a contactless power transfer system formed in accordance with an alternative embodiment of the present invention.

FIG. 7 illustrates a side view of a contactless power transfer system 350 formed in accordance with an alternative embodiment. The system 350 includes a stationary member 352 and a rotating member 354. The stationary member 352 includes a stationary platter 302 that holds inner and outer stationary cores 358 and 359 concentric with one another and in a plane extending perpendicular to an axis 356. The stationary cores 358 and 359 are E-shaped and contain corresponding inner and outer primary windings 376 and 377 arranged in concentric circles. The rotating member 354 includes a rotating platter 304 configured to rotate about axis 356 within a plane perpendicular to axis 356. The rotating platter 304 is located immediately adjacent, and rotates relative, to the stationary platter 302. The rotating platter 304 is spaced apart from the stationary platter 302 by an air gap 362. The rotating platter 304 includes inner and outer rotating cores 360 and 361, containing inner and outer secondary windings 378 and 379, each of which is partitioned into sets of sub-windings.

Figure 8:
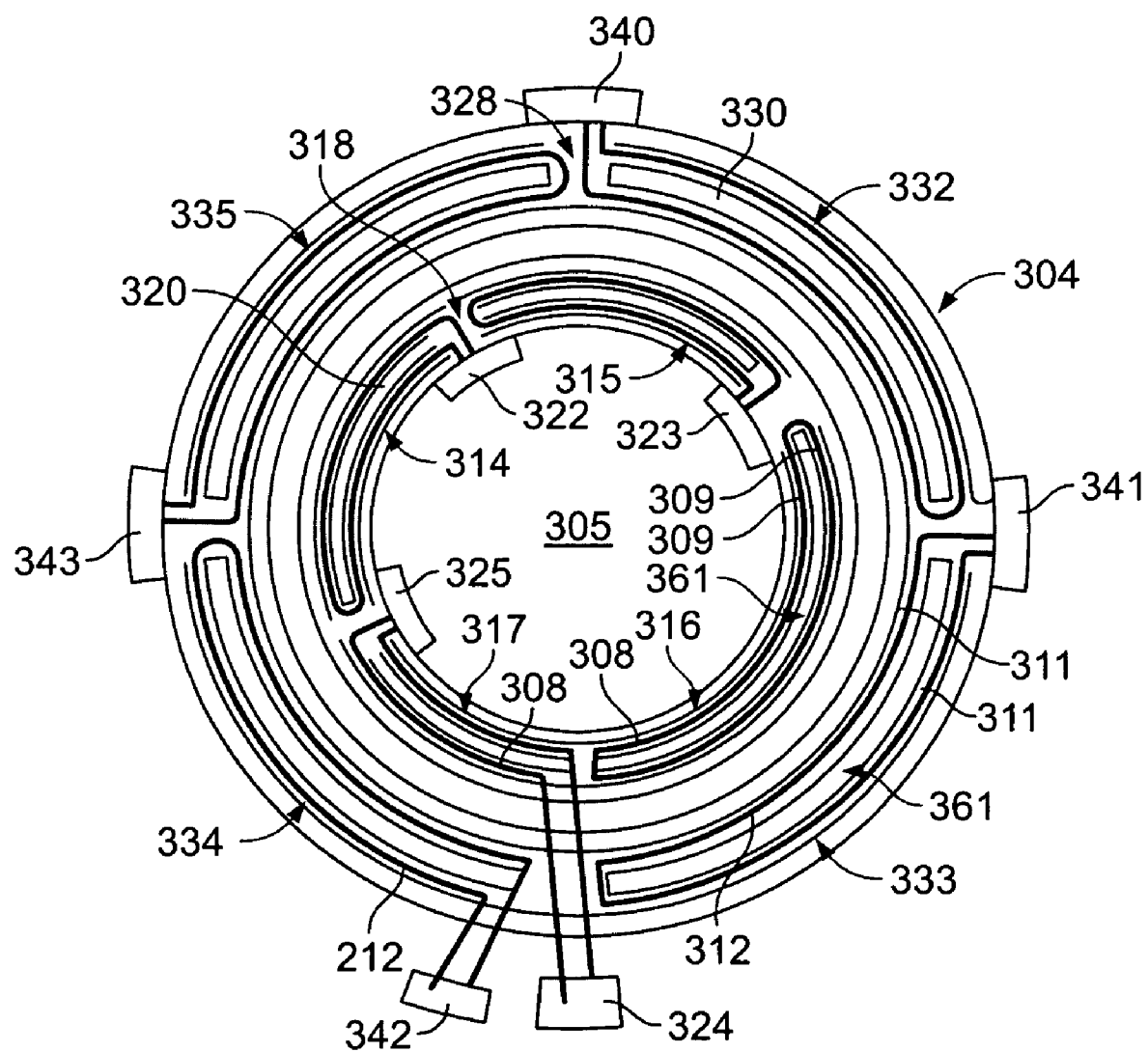
FIG. 8 illustrates the secondary winding of the rotary transformer of FIG. 7.

FIG. 8 illustrates a front view of the rotating platter 304. The rotating platter 304 is circular with an open central area 305. FIG. 8 better illustrates the inner and outer rotating cores 360 and 361 arranged radially concentric with one another. The inner rotating core 360 includes a pair of radially concentric winding slots 309, while the outer rotating core 361 includes a pair of radially concentric winding slots 311. The winding slots 309 of the inner rotating core 360 receive the wires 308 that collectively form the inner secondary winding 378. The wires 308 are wrapped about portions of the inner rotating core 308 to form sub-windings 314–317. The inner core 308 includes bridge cutouts or gaps 318 dividing the middle leg 320 into arcuate sections about which corresponding sub-windings 314–317 are formed. Each sub-winding 314–317 is joined to a corresponding signal conditioning module 322–325, respectively. The signal conditioning modules 322–325 may perform various functions, such as rectifying, doubling and filtering the signals induced into the corresponding sub-windings 314–317.

In the example of FIG. 8, the outer rotating core 361 is also divided at gaps 328 between portions of the middle leg 330. The wires 312 are divided into sub-windings 332–335 that wrap about corresponding portions of the middle leg 330 and cross at gaps 328. Each sub-winding 332–335 is joined to a corresponding signal conditioning module 340–343 which performs rectification, doubling, filtering and the like. Optionally, the number and spacing of the sub-windings may be varied. For example, the inner rotating core 360 may include only two sub-windings or more than four sub-windings. Similarly, the outer rotating core 361 may include two sub-windings or more that four sub-windings. In the example of FIG. 8, the number of sub-windings within the inner and outer cores 360 and 361 are equal at four sub-windings for each core. However, optionally the outer rotating core 361 may have fewer or more sub-windings than provided in the inner rotating core 360.

In the example of FIG. 8, the sub-windings 314–317 and the sub-windings 332–335 are combined to form a high voltage output signal, such as used to drive an x-ray source. However, optionally, only one of the inner and outer rotating cores 360 and 361 may be utilized for generating the high voltage output signal. In this example, the outer rotating core 361 may be utilized to generate the high voltage output signal, while the inner rotating core 360 is utilized to form a low voltage output signal distinct and separate from the output signal of the outer rotating core 361. As an example, the outer rotating core 361 may generate a high voltage signal at 100,000 volts or more, while the inner rotating core 360 generates a low voltage signal of less than or equal to 1,000 volts. Optionally, the inner rotating core 360 may include a single winding, and not be broken into sub-windings, when utilized to generate the low voltage output signal. The low voltage output signal may be utilized to drive electronic components mounted on the rotating platter 304.

Figure 9:
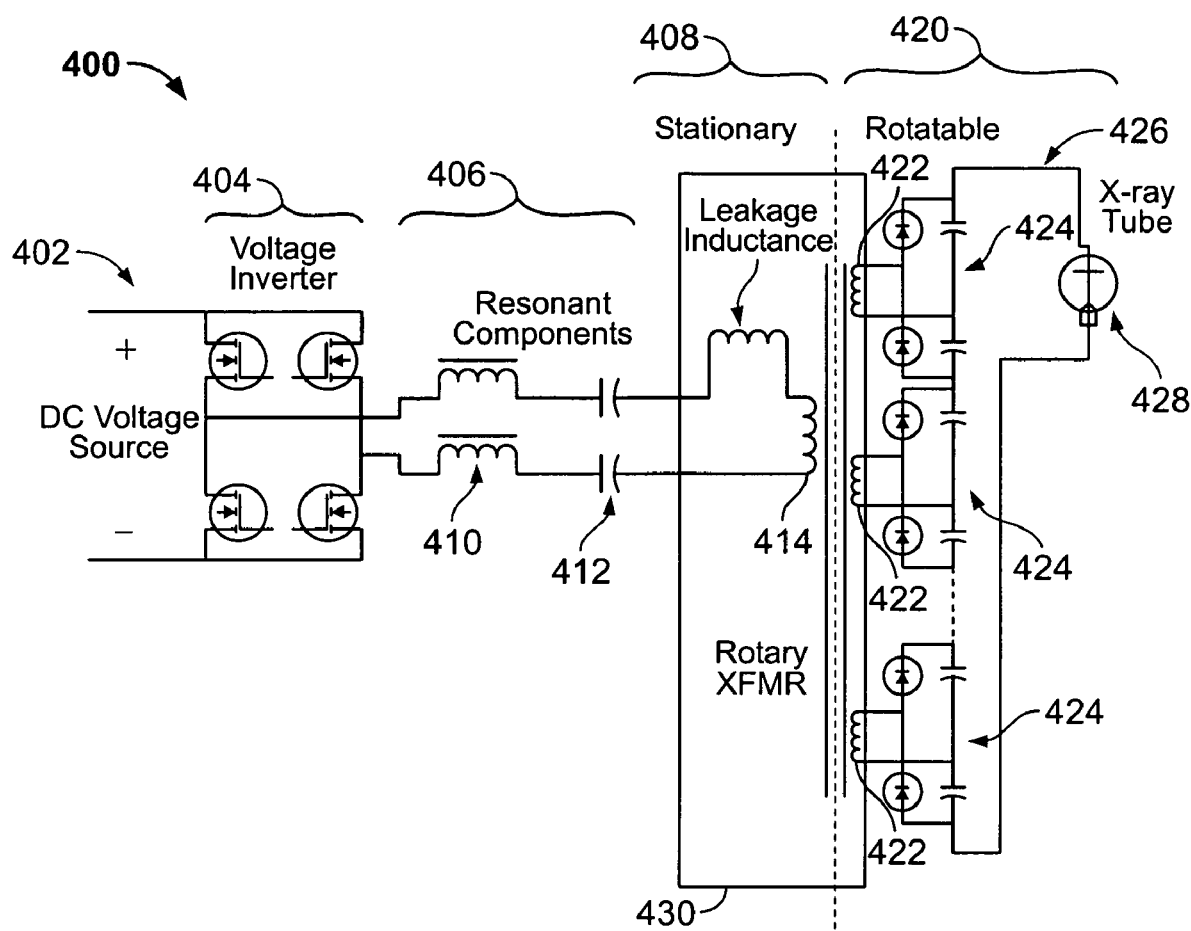
FIG. 9 illustrates a schematic circuit diagram of a contactless power transfer system formed in accordance with an embodiment of the present invention.

FIG. 9 illustrates a schematic representation of a contactless power transfer system 400 having a DC voltage source 402 joined with a voltage inverter 404 that converts an incoming DC voltage to an AC voltage. An output from the voltage inverter 404 is passed through resonant components 406 to a stationary portion 408 of the system 400. The resonant components 406 may include in doublers 410 and resonant capacitors 412. The resonant capacitors 412 are provided on the primary side of the system 400. The stationary portion 408 includes a primary winding 414 that is held in a stationary core (such as described above).

The system 400 further includes a rotating portion 420 that includes a rotating core (described above in connection with FIGS. 1–8). The rotating portion 420 is divided into arcuate portions, each arcuate portion of which contains an independent sub-winding 422. Each sub-winding 422 is electrically joined to a corresponding signal conditioning module 424. The signal conditioning module 424 are joined in series to produce a high-voltage output 426 that is configured to be supplied to a high-voltage component 428 (e.g. in x-ray source and the like). The primary winding 414 and the secondary sub-windings 422 cooperate to collectively defined a rotary transformer as denoted within block 430.

Figure 10:
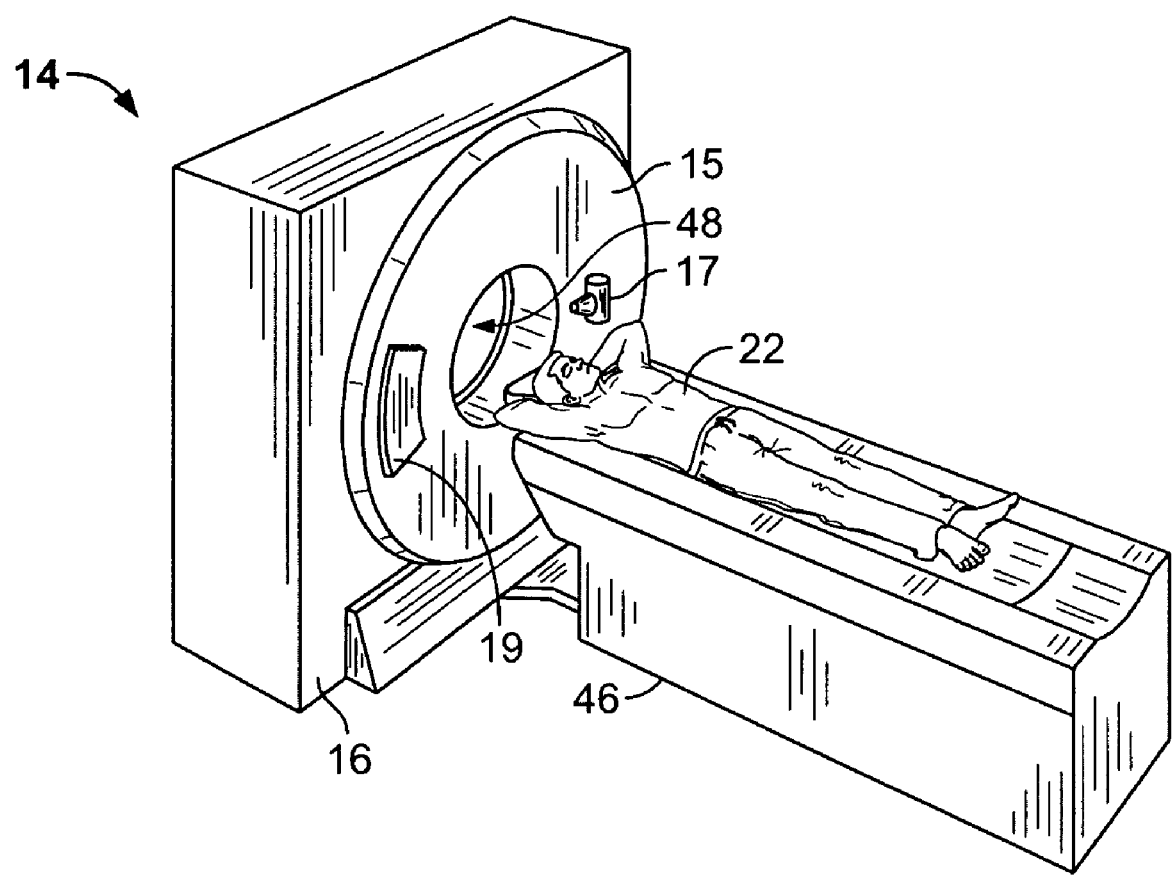
FIG. 10 illustrates a computed tomography (CT) system implementing a contactless power transfer system in accordance with an embodiment of the present invention.
Figure 11:
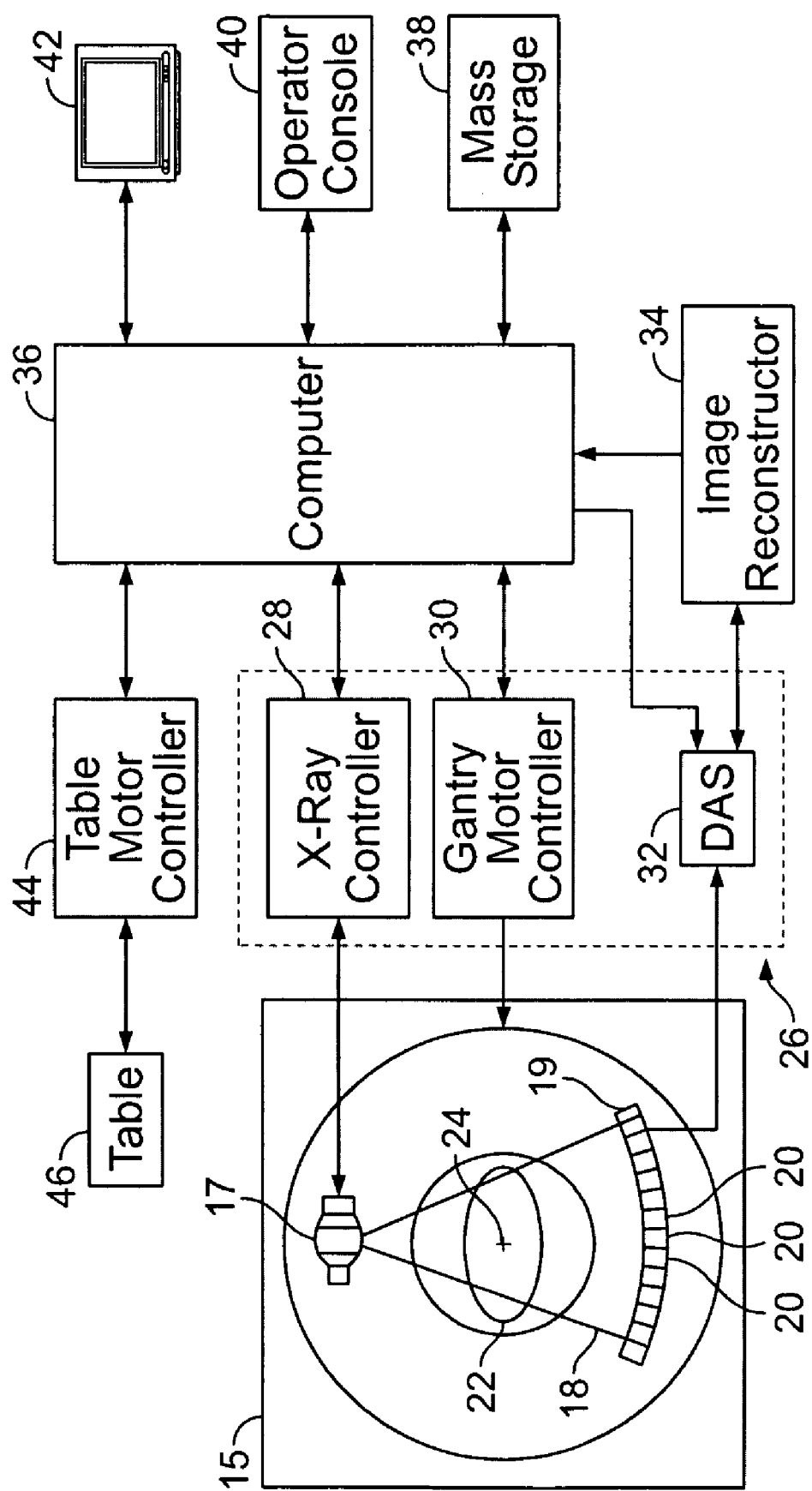
FIG. 11 illustrates a block diagram of the computed tomography system of FIG. 10.

FIGS. 10 and 11 illustrate a computed tomography (CT) imaging system 14 including a rotatable gantry 15. Gantry 15 is positioned in a gantry support 16 and has an x-ray tube 17 that projects a beam of x-rays 18 toward a detector array 19 on the opposite side of the gantry 15. Gantry 15 is designed to rotate and, as such, is defined as a rotating side whereas support 16 does not rotate and, as such, is defined as a stationary side. The gantry 15 implements a contactless power transfer system as described above in connection with FIGS. 1–9. The rotating base is designed to support x-ray tube 17 and other auxiliary components (not shown) during rotation around a medical patient 22. One skilled in the art will appreciate that embodiments of the present invention are also applicable to the projection and detection of gamma rays and other HF electromagnetic energy.

Detector array 19 is formed by a plurality of detectors 20 which together sense the projected x-rays that pass through the medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 15 and the operation of x-ray source 17 are governed by a control mechanism 26 of CT system 14. Control mechanism 26 includes an x-ray controller 28 that provides power and timing signals to an x-ray source 17 and a gantry motor controller 30 that controls the rotational speed and position of gantry 15. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 15. Particularly, table 46 moves portions of patient 22 through a gantry opening 48.

Figure 12:
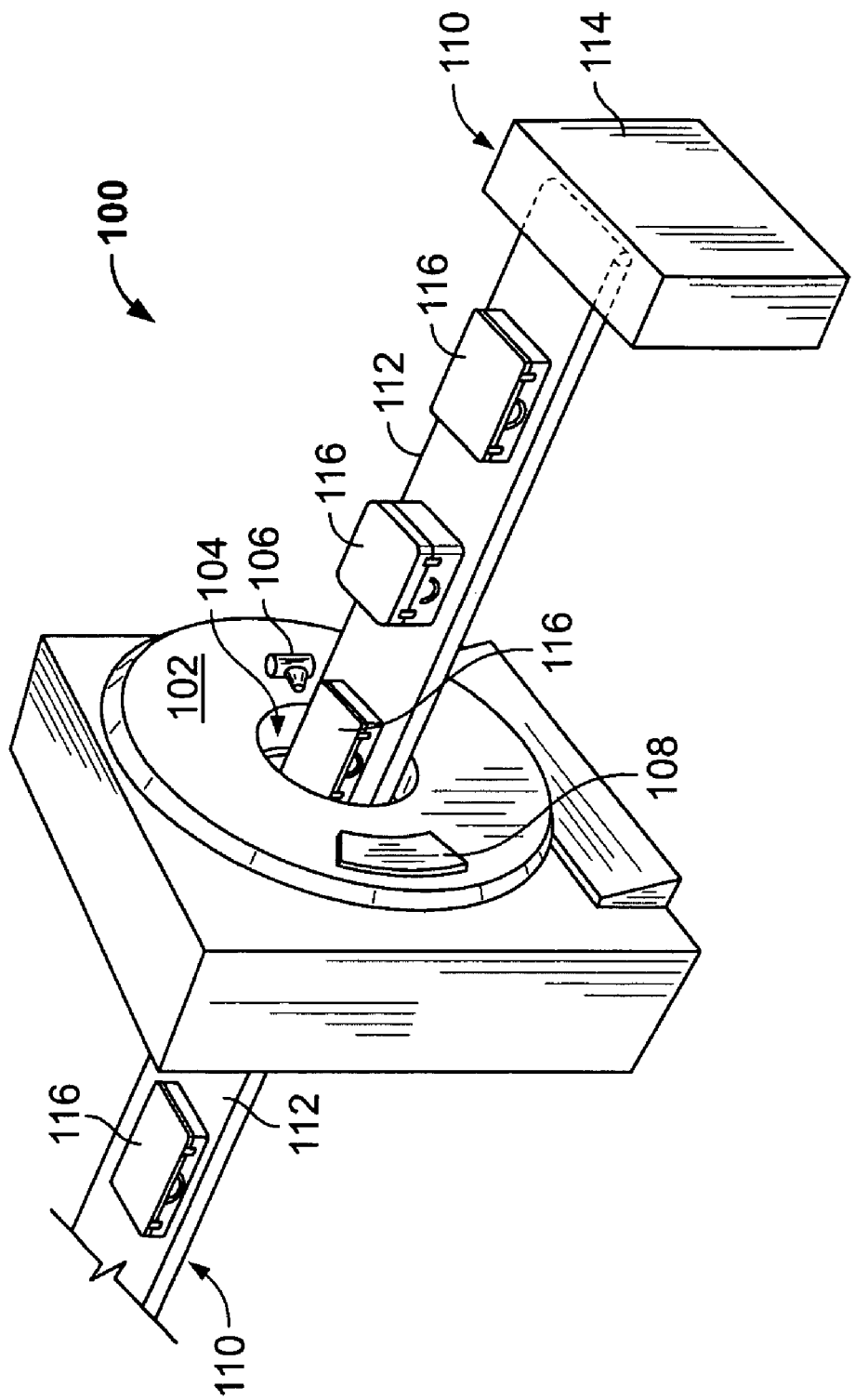
FIG. 12 illustrates a baggage scanning system implementing a contactless power transfer system in accordance with an embodiment of the present invention.

FIG. 12 illustrates a package/baggage inspection system 100 incorporating a contactless power transfer system formed in accordance with an embodiment of the present invention. The system 100 includes a rotatable gantry 102 having an opening 104 therein through which packages or pieces of baggage may pass. The rotatable gantry 102 houses a high frequency electromagnetic energy source 106 as well as a detector assembly 108. A conveyor system 110 is also provided and includes a conveyor belt 112 supported by structure 114 to automatically and continuously pass packages or baggage pieces 116 through opening 104 to be scanned. Objects 116 are fed through opening 104 by conveyor belt 112, imaging data is then acquired, and the conveyor belt 112 removes the packages 116 from opening 104 in a controlled and continuous manner. As a result, postal inspectors, baggage handlers, and other security personnel may non-invasively inspect the contents of packages 116 for explosives, knives, guns, contraband, etc.

For example, only 2 turns per secondary winding may be used. Alternatively, there may be approximately 100 turns per secondary sub-winding in order to produce ~160 kV DC (assuming a 2 turn primary winding and 4 secondary sub-windings). There are also a plurality of rectifier/doublers placed around the core. In certain embodiments, these rectifier/doublers may be placed at 90 deg intervals although other intervals may be used. The equation below illustrates the turn relationship:

$$Vout = 2 \cdot Vin \cdot \frac{\# \ turns_{sec}}{\# \ turns_{pri}} \cdot \# \ sec$$

$$Vout = 2 \cdot 400[V] \cdot \frac{100}{2} \cdot 4 = 160[kV]$$

where the coefficient of (2) is due to the effect of the voltage rectifier/doubler circuit.

By increasing the number of secondary sub-windings (#sec), the AC voltage on each winding is reduced, thereby reducing high frequency capacitive loading to ground or other circuits. For example, if #sec=4, each winding may have 40 kV AC present (at the inverter frequency). Optionally, the number of secondary sub-windings may be increased (e.g., #sec=8). With 8 secondary sub-windings, each winding may have only 20 kV AC present, thereby reducing the capacitive currents by a factor of 2.

In the above examples, the windings are wound azimuthally and loop around the middle leg of an E-shaped highly permeable material (e.g. E-core ferrite), such that the planes (or curved planes) formed by the windings face each other. Certain of the above geometries minimize the distance between primary and secondary windings; maximize magnetic field cancellation between primary and secondary windings; and reduce transformer leakage inductance. Stray EMI is limited to the vicinity of the windings. An insulator separates the high voltage potential of the secondary sub-windings from the E-cores. On the outside of the insulator is a conductive layer may be provided and attached to ground potential for safety. The shield is segmented so as to not form a conductive loop.

The above described contactless power transfer systems eliminate the contact slip ring brushes, associated dust, wear-out, and preventive maintenance which results in advantageous cost savings. This results in a direct reduction in the mass from the rotating frame of the gantry or system. Also, a counter-balance may be removed from the rotating frame. Eliminating the HV Tank provides more room on the rotating member to eliminate cantilevered components so as to have a much more uniformly balanced gantry. A further cost reduction stems from the placement of the inverter(s) and auxiliary DC—DC converters on the stationary side of the frame. Moreover, by having multiple secondary windings on the rotary transformer results in a reduction in the complexity, number of parts, and volume of the system. The system provides reduced radiated electromagnetic emissions as a result of the split impedance in the inverter output legs and the configuration of the rotary transformer core.

While the above embodiments are described with cores having an E-shaped cross-section, optionally other cross-sections may be utilized. For example, the cores may have a C-shaped or U-shaped cross-section, with the secondary sub-windings wrapped about one or both of the posts on opposite ends of the C-shaped or U-shaped core.

While the invention has been described in terms of various specific embodiments, those skilled in the art will recognize that the embodiments described can be practiced with modification within the spirit and scope of the claims.

What is claimed is:

1. A contactless power transfer system, comprising:
   a stationary member including a power input configured to receive power at a first voltage from a power supply;
   a rotating member rotatably coupled to the stationary member; and
   a rotary transformer having primary and secondary sides, the primary side being disposed on the stationary member and having a primary winding configured to receive power at the first voltage from the power input, the secondary side being disposed on the rotating member and configured to produce power at the second voltage, the secondary side having a rotating core and separate secondary sub-windings, each said sub-winding including a forward path and a return path circumferentially disposed along the rotating core, the forward path and return path of each said sub-winding rotating proximate to and spaced a substantially equal distance from the primary winding disposed on the stationary member.

2. The power transfer system of claim 1, further comprising a high voltage (HV) component disposed on the rotating member, the secondary side providing the power at a high voltage to the HV component.

3. The power transfer system of claim 1, wherein the rotating core includes an E-shaped cross-section divided into at least two arcuate sections, each of the sub-windings being wrapped about a separate and corresponding one of the arcuate sections.

4. The power transfer system of claim 1, further comprising a gantry coupling the stationary and rotating members to one another.

5. The power transfer system of claim 1, further comprising separate signal conditioning modules, each of which is joined to output leads of a corresponding one of the sub-windings.

6. The power transfer system of claim 1, wherein each of the sub-windings has corresponding sub-winding output leads that output power at a low voltage, the low voltage being less than the second voltage at which the power is output from the secondary side.

7. The power transfer system of claim 1, wherein each of the sub windings has corresponding sub-winding output leads that output power, the power from the sub-winding output leads being combined to form a high voltage power output from the secondary side.

8. The power transfer system of claim 1, wherein each of the sub-windings has corresponding sub-winding output leads that output power, the power from one of the sub-windings constituting the power output by the secondary side as the second voltage.

9. The power transfer system of claim 1, further comprising separate rectifier circuits disposed on and distributed about the rotating member, the separate/rectifier circuits being joined to the separate sub-windings.

10. The power transfer system of claim 1, further comprising separate rectifier circuits joined to each of the sub-windings.

11. The power transfer system of claim 1, wherein the contactless power transfer system is implemented in one of a CT system and a baggage scanning system.

12. The power transfer system of claim 1, further comprising an x-ray source and detectors provided on the rotating member, the secondary side providing high voltage power to the x-ray source and low voltage power to the detector.

13. The power transfer system of claim 1, wherein the forward and return paths in each of the sub-windings forms a closed loop entirely contained within an arcuate section of the rotating core, the forward and return paths being aligned in a common plane defined by a side of the rotating core.

14. The power transfer system of claim 1, wherein each of the sub-windings forms a closed loop having ends located proximate ends of adjacent sub-windings.

15. The power transfer system of claim 1, wherein each of the sub-windings extends over a separate and independent arcuate section of the rotating core.

16. An x-ray scanning system, comprising:
a gantry having a stationary member coupled to a rotating member, the rotating member having an opened area proximate an axis about which the rotating member rotates;
an x-ray source provided on the rotating member;
a power supply configured to provide power at a first voltage; and
a rotary transformer having primary and secondary sides, the primary side being disposed on the stationary member and having a primary winding that receives power at the first voltage from the power supply, the secondary side being disposed on the rotating member and producing power at a second voltage, the secondary side having a rotating core and separate secondary sub-windings, each said sub-winding including a forward path and a return path circumferentially disposed along the rotating core, the forward and return paths of each of the sub-windings rotating proximate to and spaced a substantially equal distance from the primary winding disposed on the stationary member.

17. The system of 16, further comprising an x-ray detector disposed on the rotating member and configured to receive x-rays from the x-ray source.

18. The system of 16, wherein the x-ray source constitutes a high-voltage (HV) component, the secondary side providing power at a high-voltage to the x-ray source.

19. The system of 16, wherein the rotating core includes an E-shaped cross-section divided into at least two arcuate sections, each of the sub-windings being wrapped about a separate and corresponding one of the arcuate sections.

20. The system of 16, further comprising separate signal conditioning modules, each of which is joined to output leads of a corresponding one of the sub-windings, the signal conditioning modules being disposed evenly about and located on the rotating member.

21. The system of 16, wherein each of the sub-windings has corresponding sub-winding output leads that output power at a low voltage, the low voltage being less than the second voltage, at which power is output from the secondary side.

22. The system of 16, wherein each of the sub-windings has corresponding sub-winding output leads that output power, the power from the sub-winding output leads being combined to form a high voltage power output by the secondary side.

23. The system of 16, wherein each of the sub-windings has corresponding sub-winding output leads that output power, the power from one of the sub-windings constituting the power output by the secondary side at the second voltage.

24. The system of 16, further comprising separate rectifier circuits disposed on, and distributed about, the rotating member, the separate rectifier circuits being joined to corresponding separate sub-windings.

25. The system of 16, further comprising separate rectifier circuits joined to each of the sub-windings.

26. The system of 16, wherein the gantry is configured to receive one of a human or animal patient and the x-ray source is configured to perform a CT scan.

27. The system of 16, wherein the gantry is configured to receive luggage and the x-ray source is configured to perform baggage scanning.

28. The system of 16, wherein the x-ray source represents a high-voltage component, the system further comprising low-voltage detectors provided on the rotating member, the secondary side providing separate high-voltage and low-voltage power outputs to the x-ray source and the detector.

29. An x-ray generator comprising:
a stationary power supply configured to provide power to a rotary transformer having E-shaped magnetically permeable cores;
the rotary transformer having a primary winding and at least two secondary windings, and configured to step-up the power received from the stationary power supply to provide a high voltage output, wherein the primary winding and the two secondary windings are wound azimuthally and circularly around a middle leg of the E-shaped magnetically permeable cores; and
a rotatable x-ray tube coupled to receive the high voltage output from the rotary transformer.

30. The x-ray generator of claim 29 further comprising a plurality of high voltage rectifier circuits circumferentially distributed around the rotary transformer and configured to rectify the high voltage output of the rotary transformer to provide a high voltage DC power to the rotatable x-ray tube.

31. The x-ray generator of claim 30 wherein the plurality of high voltage rectifier circuits are connected in series.

32. The x-ray generator of claim 30 incorporated into a baggage/parcel inspection system.

33. The x-ray generator of claim 29 wherein the stationary power supply includes a voltage inverter having two outputs configured to provide a high voltage AC input to the rotary transformer through a pair of resonance circuits.

34. The x-ray generator of claim 29 wherein the rotary transformer further includes a segmented conductor shield that covers the at least two secondary windings, and prevents current flow in a circular manner.

35. The x-ray generator of claim 29 wherein the rotary transformer further includes a number of turns per secondary winding to provide at least a 160 kV output.

36. The x-ray generator of claim 29 incorporated into a CT system.

* * * * *